United States Patent [19]

Dousse et al.

[11] Patent Number: 4,612,395
[45] Date of Patent: Sep. 16, 1986

[54] PROCESS FOR THE PRODUCTION OF N-(2-METHYL-4-CHLOROPHENYL)-FORMAMIDINE DERIVATIVES

[75] Inventors: Roland Dousse; Raoul Nebel, both of Monthey, Switzerland

[73] Assignee: Ciba-Geigy Corporation, Ardsley, N.Y.

[21] Appl. No.: 932,830

[22] Filed: Aug. 11, 1978

Related U.S. Application Data

[63] Continuation of Ser. No. 826,807, Aug. 22, 1977, abandoned, which is a continuation of Ser. No. 662,305, Mar. 1, 1976, abandoned.

[51] Int. Cl.$^4$ .......................................... C07C 123/00
[52] U.S. Cl. ..................................................... 564/245
[58] Field of Search .................. 260/564 RF; 564/245

[56] References Cited

U.S. PATENT DOCUMENTS

| | | | |
|---|---|---|---|
| 3,394,397 | 7/1968 | Duerr et al. | 260/564 RF |
| 3,502,720 | 3/1970 | Arndt et al. | 260/564 RF |
| 3,911,012 | 10/1975 | Krieger et al. | 260/564 RF |
| 4,169,852 | 10/1979 | Landauer | 564/245 |

FOREIGN PATENT DOCUMENTS

2417669  10/1975  Fed. Rep. of Germany ...... 260/564 RF

Primary Examiner—Natalie Trousof
Assistant Examiner—L. Hendriksen
Attorney, Agent, or Firm—Karl F. Jorda; Bruce M. Collins

[57] ABSTRACT

A process for the production of N-(2-methyl-4-chlorophenyl)-formamidine derivatives of formula

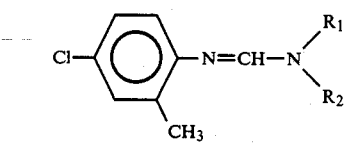

wherein $R_1$ is hydrogen or an alkyl radical having 1 to 4 carbon atoms and $R_2$ is an alkyl radical having 1 to 4 carbon atoms is disclosed which comprises reacting an N-substituted formamide with an inorganic acid chloride, such as phosphorus oxychloride, thionylchloride and phosgene, condensing the intermediate formed with o-toluidine and subsequently chlorinating the N-(2-methylphenyl)-formamidine derivative formed, all reaction steps involved in said process being carried out in the same solvent which is selected from the group of halogenated hydrocarbons.

4 Claims, No Drawings

PROCESS FOR THE PRODUCTION OF N-(2-METHYL-4-CHLOROPHENYL)-FORMAMIDINE DERIVATIVES

This is a continuation of application Ser. No. 826,807 filed on Aug. 22, 1977, which is a continuation of Ser. No. 662,305 filed Mar. 1, 1976, both now abandoned.

The present invention relates to a process for the production of N-(2-methyl-4-chlorophenyl)-formamidine derivatives of formula I

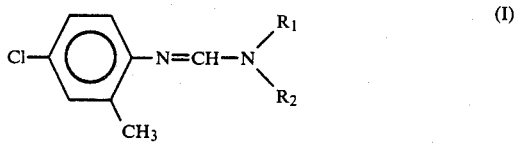

wherein $R_1$ is hydrogen or an alkyl radical having 1 to 4 carbon atoms, and $R_2$ is an alkyl radical of 1 to 4 carbon atoms.

The N-(2-methyl-4-chlorophenyl)-formamidine derivatives of formula I possess a strong selective toxicity against acarids in all stages of development as it is described in detail in U.S. Pat. Nos. 3.378.437 and 3.502.720. According to a method known from the afore-mentioned patents the N-(2-methyl-4-chlorophenyl)-formamidine derivatives of formula I are prepared by reacting an alkylformamide of formula II

wherein $R_1$ and $R_2$ have the meaning given above, with phosphorus oxychloride to form a salt like intermediate which is, without isolation, immediately further reacted with 2-amino-5-chlorotoluene to the desired N-(2-methyl-4-chlorophenyl)-formamidine derivatives of formula I. The structure of the salt-like intermediate formed by reaction of an alkylformamide of formula II and phosphorus oxychloride most likely corresponds to formula

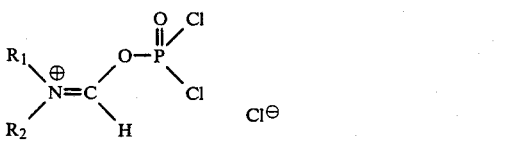

as it is described by H. Bredereck et al in Chem. Ber. 92, 837–849 (1959). Since other acid halogenides are reported to form analogous products formula III

wherein $R_1$ and $R_2$ have the meaning given above and Ac is an acyl group which corresponds to the acid chloride used, will be ascribed to the salt-like intermediates referred to in this specification.

The known process referred to above is disadvantageous in that the 2-amino-5-chlorotoluene needed as intermediate has to be prepared from o-toluidine in a multistep process. According to this process o-toluidine is converted into its N-acyl compound, for example by reaction with acetyl chloride. The 2-acetylamino-toluene this obtained is then chlorinated to form 2-acetylamino-5-chlorotoluene which is hydrolysed to 2-amino-5-chlorotoluene. This process has the further disadvantage that large quantities of by-products, namely 2-acetylamino-3-chlorotoluene and 2-acetylamino-3,5-dichlorotoluene, are formed on chlorination of 2-acetylaminotoluene which have to be separated from the desired product together with unchlorinated product.

In view of these difficulties encountered in the preparation of 2-amino-5-chlorotoluene is has already been proposed to prepare the N-(2-methyl-4-chlorophenyl)-formamidine derivatives of formula I by chlorination of the corresponding N-(2-methylphenyl)-formamidine derivatives which in turn are obtained according to the afore-mentioned method by reacting an alkylformamide of formula II with phosphorus oxychloride and further reacting the salt-like intermediate formed with o-toluidine. According to this method described in U.S. Pat. No. 3,911,012 the chlorination of N-(2-methylphenyl)-N,N-dialkylformamidines is preferably performed in an aqueous reaction medium. Further, it is mentioned that the chlorination can also be performed in organic solvents such as alcohols or glacial acetic acid.

This process is objectionable in that the preparation of the salt-like intermediate obtained by reaction of an alkylformamide of formula II with phosphorus oxychloride and/or the preparation of the N-(2-methylphenyl)-N',N'-dialkylformamidine and the chlorination must be carried out in different solvents, and, as a consequence thereof, at least one of these products must be isolated and transferred into another solvent. Further, if the chlorination is carried out in glacial acetic acid additional alkali metal hydroxide is neccessary to neutralize the reaction mixture in order to make the isolation of the chlorinated product possible.

It is, therefore, the object of the present invention to provide a process for the production of N-(2-methyl-4-chlorophenyl)-formamidine derivatives of formula I in which all reaction steps involved, namely formation of the salt-like intermediate, condensation of this intermediate with o-toluidine to a N-(2-methylphenyl)-formamidine derivative and chlorination of the latter to the desired N-(2-methyl-4-chlorophenyl)-formamidine derivative of formula I, can be performed in the same solvent.

Particularly, it is the object of the present invention to provide a process for the production of N-(2-methyl-4-chlorophenyl)-formamidine derivatives of formula I in which all reaction steps involved are performed in the same solvent in which all the intermediates formed are soluble, i.e. the whole process is performed in a homogeneous reaction medium.

It has been found that all reaction steps involved in the production of N-(2-methyl-4-chlorophenyl)-formamidine derivatives of formula I can be performed in a solvent selected from the group of halogenated hydrocarbons. Accordingly, the present invention comprises a process for the production of N-(2-methyl-4-chlorophenyl)-formamidine derivatives of formula I wherein the steps of reacting an alkylformamide of formula II

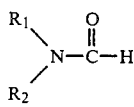

(II)

with an inorganic acid chloride selected from the group consisting of phosphorus oxychloride, thionylchloride and phosgene to form a salt-like intermediate of formula IIIa

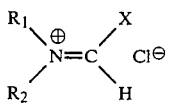

(IIIa)

wherein X represents —O—POCl$_2$, —OSOCl or chlorine, condensing this intermediate with o-toluidine and chlorinating the hydrochloride of the N-(2-methylphenyl)-formamidine derivative formed to a N-(2-methyl-4-chlorophenyl)-formamidine derivative of formula I are performed in the same solvent which is selected from the group of halogenated hydrocarbons.

Suitable halogenated hydrocarbons are for example 1.2-dichloroethane 1.1.1-trichloroethane, tetrachloroethane, chlorobenzene, o-dichlorobenzene, carbontetrachloride and, preferably chloroform.

Among the inorganic acid chlorides mentioned above phosgene is preferred. The salt-like intermediate primarily formed by reacting phosgene with an alkylformamide of formula II corresponds to formula III, wherein Ac is —COCl. However, this product is instable under the reaction conditions and decomposes according to the equation:

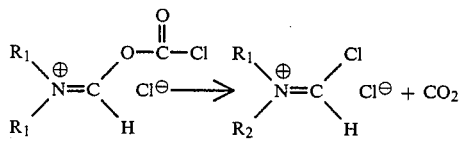

The salt-like intermediate of formula IIIa is formed by reacting an alkylformamide of formula II with one of the afore-mentioned acid chlorides, preferably with phosgene, in one of the afore-mentioned halogenated hydrocarbons, preferably in chloroform, at a temperature within the range of from −10° to +50° C., preferably from 10° to 30° C. The molar ratio of acid chloride to alkyl formamide of formula II is essentially 1:1. However, each of the reactants can be used in excess of up to 20 mol %. The molar ratio of phosgene to alkylformamide of formula II is preferably 0.95 to 0.98:1.

The condensation of a salt-like intermediate of formula IIIa with o-toluidine is carried out at a temperature of from 0° to 60° C. preferably 20° to 40° C. It is favorable to employ an excess salt-like intermediate of formula IIIa in order to complete the reaction. The chlorination of the hydrochlorides of the N-(2-methylphenyl)-formamidine derivatives formed by condensation of a salt of formula II with a dialkylformamide of formula III is carried out at a temperature of from 0° to 80° C., preferably 5° to 25° C. The chlorination is preferably effected with chlorine gas. However other chlorinating agents, such as hypchlorites and N-chloro compounds, can also be used. According to a preferred embodiment of the present invention the N-(2-methyl-4-chlorophenyl)-formamidine derivatives of formula I are prepared by reacting phosgene with an alkylformamide of formula II in a molar ratio of 0.95-0.98:1 at a temperature of 10° to 30° C. in chloroform to form a salt-like intermediate of formula IIIa, wherein X is chlorine, condensing this intermediate at 20° to 40° C. with o-toluidine and subsequently chlorinating the hydrochloride of the N-(2-methylphenyl)-formamidine derivative formed at a temperature of from 5° to 25° C.

The N-(2-methyl-4-chlorophenyl)-formamidine derivatives of formula I can be isolated from the reaction mixture in the usual way, for example by adding an aqueous solution of an alkali metal hydroxide to the reaction mixture, separating the two layers formed and evaporating the solvent from the organic layer to obtain the free N-(2-methyl-4-chlorophenyl)-formamidine derivative of formula I. On the other hand if phosgene or thionyl chloride was used for the formation of the salt-like intermediate of formula IIIa, it is also possible to remove the solvent completely or partially from the reaction mixture to obtain the crystaline hydrochloride of a N-(2-methyl-4-chlorophenyl)-formamidine derivative or to extract the reaction mixture with water to obtain an aqueous solution of the hydrochloride of an N-(2-methyl-4-chlorophenyl)-formamidine derivative of formula I. The process according to the present invention is particularly suitable for the production of N-(2-methyl-4-chlorophenyl)-N',N'-dimethylformamidine and N-(2-methyl-4-chlorophenyl)-N'-methyl-N'-n-butylformamidine.

The main advantage of the process according to the invention over the previously known methods is that all operations involved can be carried out in the same solvent. Additional advantages are gained if the whole process is performed in chloroform which is the preferred solvent according to the present invention and with phosgene as acid chloride which is also preferred. If carried out in chloroform the whole process can be performed in a homogeneous reaction medium because all intermediates and the final products present as hydrochlorides are soluble in the reaction mixture. This is particularly advantageous for the continuous performance of the process. Further, solvent losses are reduced to a minimum because chloroform is readily absorbed in dialkylformamides of formula II. Therefore, the carbon dioxide emerging from the reaction mixture which is saturated with chloroform can be treated with the alkylformamide of formula II which is subsequently transformed into the salt-like intermediate of formula IIIa to absorb the chloroform. This is both an economical advantage as well as ecological advantage.

The process according to the present invention is further illustrated by the following examples.

EXAMPLE 1

At a temperature of 18°–22° C. 99 kg (1000 moles) of phosgene are introduced into a solution of 74,5 kg (1019 moles) of dimethylformamide in 360 kg dry chloroform which is placed in an enamelled reaction vessel provided with a stirrer. The carbon dioxide emerging from the reaction mixture is freed from chloroform and traces of phosgene by washing with dimethylformamide. Then 101, 3 kg (945 moles) of o-toluidine are introduced into the homogeneous solution obtained within two hours at an inner temperature of 22°–27° C. After addition of the o-toluidine the homogeneous solution formed is stirred for 30 minutes. Thereafter, at a temperature of 15°–20° C. 67 kg (945 moles) of chlorine are introduced within 4 hours. During the addition of chlorine the pressure in the reaction vessel increases from 1 atmosphere to 1.3 atmospheres. After addition of the chlorine the homogeneous solution is stirred for one hour. Thereafter 150 kg of water are added whereby two layers are formed. After separation the aqueous layer is heated to 100°–105° C. to remove residual chloroform and excess hydrogen chloride. Then a 25% aqueous sodium hydroxide solution is added the cooled solution until a pH value of 11 is reached. The crude oily product is separated and purified by fractional distillation. There are obtained:

7.7 kg (5% of the theoretical amount) of N-(2-methylphenyl)-N',N'-dimethylformamidine, b.p. 128°–130° C./11 torr.

11.0 kg (5% of the theoretical amount) of N-(2-methyl-6-chlorophenyl)-N',N'-dimethylformamidine, b.p. 144°–146° C./11 torr.

147.0 kg (80% of the theoretical amount) of N-(2-methyl-4-chlorophenyl)-N'N'-dimethylformamidine b.p. 159°–161° C./11 torr.

It is also possible to isolate the N-(2-methyl-4-chlorophenyl)-N',N'-dimethylformamidine as hydrochloride. For this purpose the third part of the chloroform present in the solution obtained after chlorination is distilled off and the same volume of xylene is added. The precipitated hydrochloride is separated by filtration, washed with xylene and dried.

EXAMPLE 2

At a temperature of 25°–30° C. 71 kg (718 moles) of phosgene are introduced within 5 hours into a solution of 54.1 kg (740 moles) of dry dimethylformamide in 280 kg of chlorobenzene which is placed in an enamelled reaction vessel provided with a stirrer. After addition of the phosgene the reaction mixture is stirred for 30 minutes at 25°–30° C. Then, at a temperature of 45°–50° C. 74 kg (690 moles) of o-toluidine are added within 2 hours and the reaction mixture is stirred for an additional hour at 75°–80° C. The mixture is cooled to 30° C. and a solution of 1 kg of triethanolamine in 1 kg of chlorobenzene is added. Subsequently the pressure in the reaction vessel is reduced to 200 torr and 52.5 kg (740 moles) of chlorine are introduced within 6 hours at 30°–35° C. in the following manner: First an amount of chlorine is introduced which is sufficient to increase the pressure in the reaction vessel to 1140 torr. Then the addition of chlorine is stopped and the mixture is stirred for 1 hour. Thereafter, the pressure is again reduced to 200 torr and the residual chlorine is introduced. After addition of the chlorine the reaction mixture is stirred for 2 hours at 30°–35° C. Then, after equalisation of the pressure 150 kg of water are added to the suspension of N-(2-methyl-4-chlorophenyl)-N',N'-dimethylformamidine hydrochloride obtained while the temperature is kept below 50° C. by cooling. Thereafter, residual chlorine is removed by addition of an aqueous sodium bisulfite solution and, after separating of the two layers a 25% aqueous solution of sodium hydroxide is added to the aqueous layer until a pH value of 11 is reached. The crude oily product is then separated and purified by fractional distillation. 115 kg (80% of the theoretical amount) of N-(2-methyl-4-chlorophenyl)-N',N'-dimethylformamidine, b.p. 141°–143° C./0.5 torr are obtained.

EXAMPLE 3

In an enamelled reaction vessel provided with a stirrer a mixture of 235 kg of chloroform, 45.5 kg (374 moles) of o-toluidine is heated to 60° C. To this solution 52 kg (437 moles) of thionylchloride are added within 1 hour while the temperature is kept at 60° C. After stirring for 1 additional hour the reaction mixture is cooled to 5°–10° C. and after addition of 0.4 kg of iodine, 37.5 kg (530 moles) of chlorine are introduced within 4 hours and the mixture obtained is stirred for additional 12 hours at 20° C. Subsequently hydrogen chloride and excess chlorine are removed by bubbling a stream of nitrogen through the reaction mixture. The whole mixture is then poured onto 140 kg of ice and 15 kg of a 24% aqueous solution of sodium bisulphite while stirring at a temperature not exceeding 15° C. After adjusting a pH value of 10–11 by addition of a 30% aqueous solution of sodium hydroxide the whole is stirred for 1 hour. Then the organic layer is separated and, after washing with 70 kg of water, the solvent is evaporated in vacuo. The crude product thus obtained is purified by distillation in vacuo. 85 kg of a product, b.p. 130°–135° C./0.5 torr are obtained containing 86% of N-(2-methyl-4-chlorophenyl)-N'-methyl-N'-n-butylformamidine 1% of N-(2-methylphenyl)-N'-methyl-N'-n-butylformamidine 7.2% of N-(2-methyl-6-chlorophenyl)-N'-methyl-N'-n-butylformamidine 2% of N-(2-methyl-4,6-dichlorophenyl)-N'-methyl-N'-n-butylformamidine 0.2% of 2-amino-5-chlorotoluene 0.2% of N-methyl-N-n-butylformamide 3% of non-identified by-products (all percentages by weight)

EXAMPLE 4

At a temperature of 20°–40° C. 370 kg of phosgene are introduced within in 3 hours into a mixture of 1150 kg of o-dichlorobenzene and 249 kg of dry dimethylformamide which is placed in an enamelled reaction vessel provided with a stirrer. After addition of the phosgene the pressure in the reaction vessel is reduced to 200 torr in order to remove unreacted phosgene. Then 300 kg of o-toluidine are added whereby care is taken that the temperature does not exceed 60° C. Subsequently the reaction mixture is heated to 80° C. and kept at this temperature for 2 hours.

Then 25 kg of triethanolamine are added and 235 kg of chlorine are introduced at a temperature of 20°–40° C. The hydrogen chloride formed during chlorination is led to a caustic soda/sodium thiosulphate scrubber. Then, after stirring the reaction mixture for two hours, 650 kg of water are added while cooling and excess chlorine present in the reaction mixture is removed by addition of sodium bisulphite. After separation of the organic phase 280 kg of toluene are added to the aqueous phase and the mixture is stirred for 10 minutes. Then, after separation of the toluene, 400 kg of fresh toluene are added and the pH value of the whole mixture is adjusted to 10 by addition of 820 kg of 30% aqueous sodium hydroxide. The addition of sodium hydroxide is made at such a rate that the whole mixture has a temperature of 35°–40° C. at the end of the addition. After addition of the sodium hydroxide the whole mixture is stirred for 2 hours at 35°–40° C. and thereafter the two layers are separated. The organic layer which contains the product is worked up by distillation. At first a water-containing fraction is obtained under slightly reduced pressure. Then the toluene is distilled off in vacuo. Finally, by raising the temperature, about 10 kg of a third fraction are obtained which consists essentially of o-dichlorobenzene. The distillation is stopped when a temperature of 145° C. at the bottom and 85°-90° C. at the head of the column is reached. The crude N-(2-methyl-4-chlorophenyl)-N',N'-dimethylformamidine obtained as residue is purified by distillation in vacuo. 455 kg (74.3% of theory) of N-(2-methyl-4-chlorophenyl)-N',N'-dimethylformamidine, b.p. 159°-161° C./11 torr are obtained.

What we claim is:

1. The process for the preparation of an N-(2-methyl-4-chlorophenyl)-N'-methyl-N'-alkylformamidine which comprises reacting, in chloroform an N-methyl-N-alkylformamide of the formula

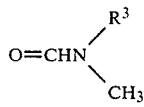

wherein $R^3$ is alkyl of up to 4 carbon atoms, with phosgene to form the adduct thereof and carbon dioxide, reacting said adduct, without isolation from said chloroform, with ortho-toluidine to form N-(2-methylphenyl)-N'-methyl-N'-alkylformamidine hydrochloride, and chlorinating said N-(2-methylphenyl)-N'-methyl-N'-alkylformamidine hydrochloride with chlorine gas without isolation from said chloroform, at a temperature of from about 0° to 80° C.

2. The process according to claim 1 wherein said N-methyl-N-alkylformamide is dimethylformamide.

3. The process according to claim 2 wherein the carbon dioxide formed is washed with dimethylformamide to remove any excess phosgene and chloroform and such dimethylformamide is thereafter used as a reactant as therein defined.

4. The process as defined in claim 2, wherein the chlorination is conducted at temperatures of from 5° to 25° C.

* * * * *